United States Patent [19]

Schneider

[11] Patent Number: 4,951,665
[45] Date of Patent: Aug. 28, 1990

[54] INSULATING, ANTI-KINKING Y CONNECTOR FOR ARTHROSCOPIC SURGERY AND METHOD OF MAKING

[75] Inventor: Barry L. Schneider, Deerfield, Ill.

[73] Assignee: Hollister Incorporated, Libertyville, Ill.

[21] Appl. No.: 308,419

[22] Filed: Feb. 8, 1989

[51] Int. Cl.$^5$ .............................................. A61F 7/00
[52] U.S. Cl. .................................... 128/400; 604/284; 165/46
[58] Field of Search ................. 604/43, 113, 114, 293, 604/284; 128/24.1, 68.1, 399, 400, 402; 138/115, 116; 165/46

[56] References Cited

U.S. PATENT DOCUMENTS

| 719,638 | 2/1903 | Batter | 604/293 |
|---|---|---|---|
| 2,587,910 | 3/1952 | Shulman | 604/284 |
| 2,885,189 | 5/1969 | MacCracken | 165/46 |
| 3,894,213 | 7/1975 | Agarwala | 128/400 |
| 3,995,621 | 12/1976 | Fletcher et al. | 128/400 |
| 4,010,795 | 3/1977 | Stenberg | 128/400 |
| 4,140,130 | 2/1979 | Storm, III | 128/400 |

FOREIGN PATENT DOCUMENTS

| 330182 | 6/1952 | Italy | 138/115 |
|---|---|---|---|
| 1448068 | 9/1976 | United Kingdom | 128/400 |

Primary Examiner—Stephen C. Pellegrino
Assistant Examiner—Ralph Lewis
Attorney, Agent, or Firm—Tilton, Fallon, Lungmus

[57] ABSTRACT

An insulating, anti-kinking Y connector for arthroscopic surgery and method of making wherein two sections of resilient double lumen tubing each having a portion of an interconnecting bight removed therefrom, are interconnected in Y configuration.

18 Claims, 1 Drawing Sheet

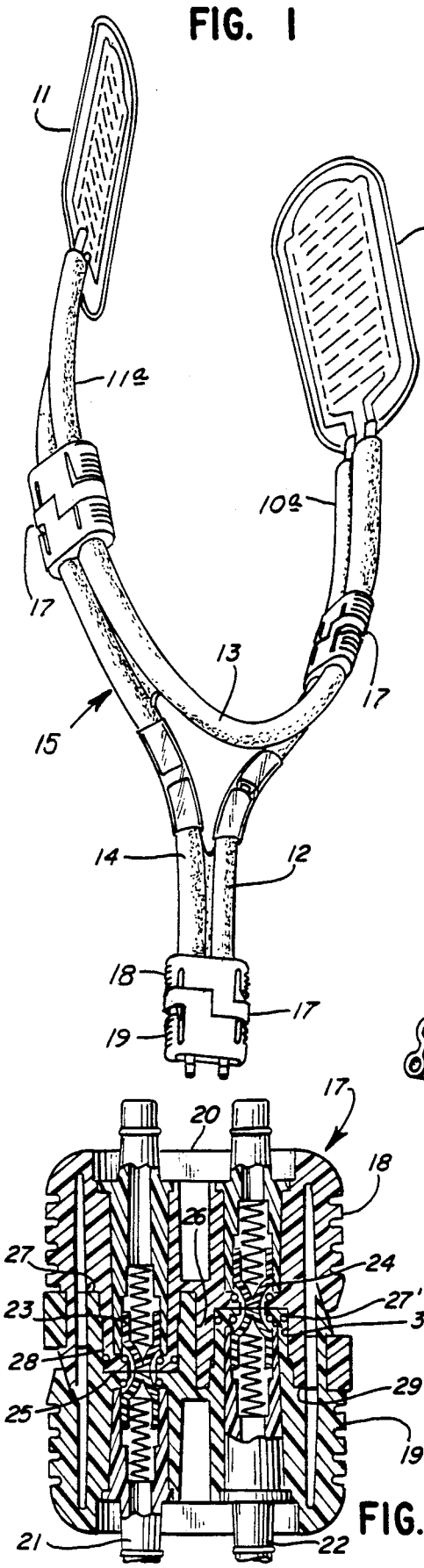
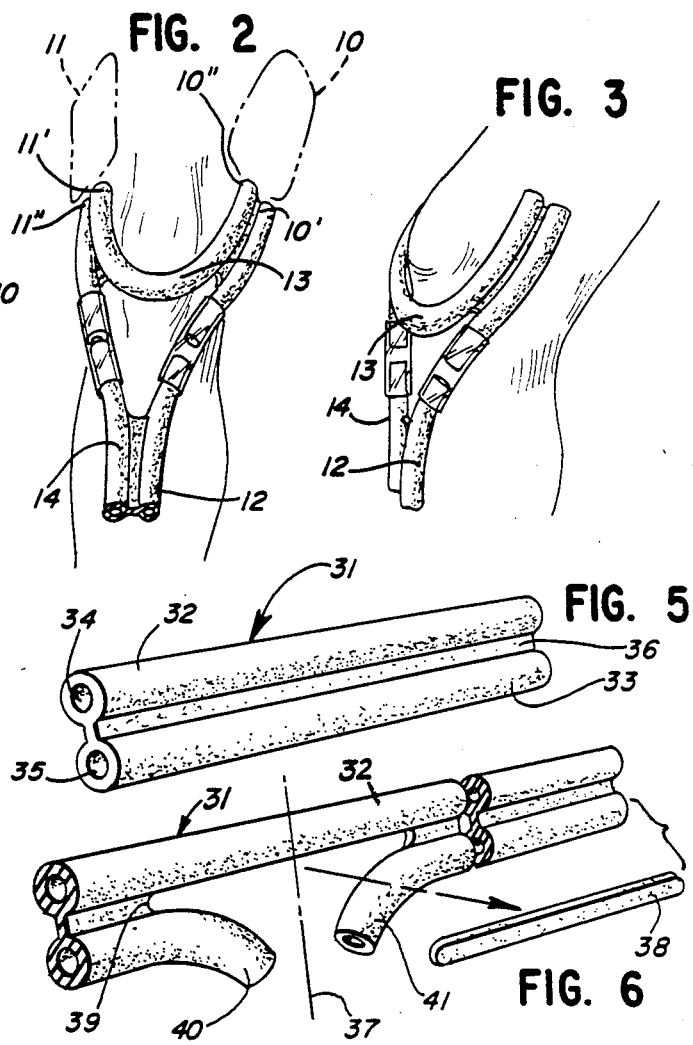
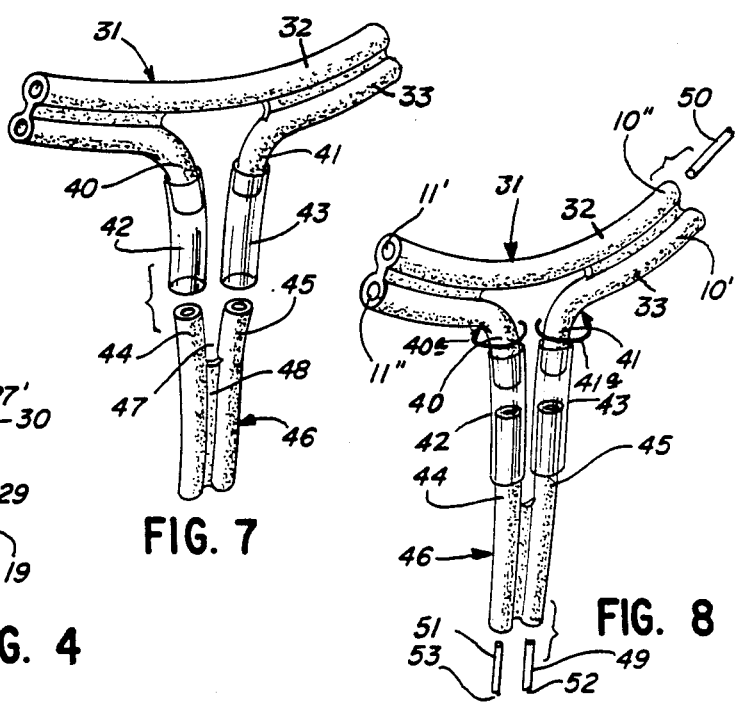

INSULATING, ANTI-KINKING Y CONNECTOR FOR ARTHROSCOPIC SURGERY AND METHOD OF MAKING

BACKGROUND AND SUMMARY OF INVENTION

This invention relates to an insulating, anti-kinking Y connector for arthroscopic surgery and method of making.

In arthroscopic surgery it is important to provide thermal treatment, either heating or cooling. In connection with knee surgery, the practice has been to provide a pair of pads for position on each side of the upper leg slightly above the knee. These pads have internal conduit means for circulating thermal fluid with the pads being connected in series and each connected to a source of the thermal fluid. One pad is connected to the supply line and the other to the return line, thereby forming, in effect, a Y configuration.

A number of problems have occurred in the provision of such treatment. A significant problem resides in the possibility of kinking of the conduit lines conducting the thermal fluid. Inasmuch as the circuit is a series circuit, a kink in any one position "starves" the entire circuit. Another problem resides in the possibility of misconnection—the supply line from the control mechanism source being connected to the return conduit means of the second "in line" pad. This also is avoided through the practice of the invention by the provision of unique hermaphroditic elements constituting the connections between the inventive Y connector and the pads.

Other objects and advantages of the invention may be seen in the details of the ensuing specification.

The invention is explained in conjunction with an illustrative embodiment in the accompanying drawing, in which FIG. 1 is a perspective view of pads equipped with the inventive Y connector and hermaphroditic couplings;

FIG. 2 is a fragmentary perspective view of the inventive Y connected installed on a person's leg around the knee, such as would be seen from the front;

FIG. 3 is a view similar to FIG. 2 but with the view taken slightly from the side;

FIG. 4 is a fragmentary view in longitudinal section of the inventive hermaphroditic coupling;

FIG. 5 is a fragmentary perspective view of the insulating, double lumen tubing employed in the practice of the invention; and FIGS. 6-8 are fragmentary perspective views of the steps performed in the making of the inventive Y connector.

DETAILED DESCRIPTION

Referring first to FIG. 1, the numeral 10 designates a first thermal pad adapted to be positioned on one side of a patient's upper leg and the numeral 11 designates a second pad. Not shown but indicated schematically is the conventionally provided fluid circuitry within each pad for the delivery and removal of the thermal fluid to and from the pad.

As can be best seen in FIGS. 2 and 3 there is a first conduit line 12 which is adapted to deliver thermal fluid from a source (not shown) to the first pad 10. A second conduit line 13 interconnects the pads 10 and 11 for series flow of the heating/cooling fluid and a third conduit line 14 constitutes the return line for the thermal fluid from the second pad 11 to the source (not shown).

Interposed in the conduit lines are three hermaphroditic couplings 17 (FIG. 1). These can be seen in greater detail in FIG. 4 where the numeral 17 designates generally the hermaphroditic coupling composed of two identical elements 18 and 19, each of which is non-symetrical when viewed in the longitudinal section of that figure. For ease of presentation, only one such element will be described. It will be seen that each element includes a block like body 20 and extending longitudinally through such body 20 are parallel passages or lumens 21 and 22 (designated at the bottom of FIG. 4). Each is equipped with a poppet-like check valve 23 and 24. The body 20 at the end thereof 25 which engages the other element 18 or 19 has a stepped end wall as at 26 with a first wall portion 27 equipped with a longitudinally extending tubular projection 28 aligned with the first lumen 21. The end 25 also includes a second wall portion 29 equipped with a longitudinally extending recess 30 aligned with the second lumen 22 and sized to receive the tubular projection 27' of the element 19. Additional details of construction and operation can be found in my co-pending application Ser. No. 07/308366, filed 2/8/89, and express reference is made thereto.

Method of Making

Reference is now made to FIGS. 5-8 which illustrate the method of making the inventive Y connector 15. In FIG. 5, the numeral 31 generally designates a first length of tubing ultimately becoming the insulating envelope for the internal conduits or tubes carrying thermal fluid. Advantageously, the length 31 is constructed of a polyurethane foam or other polymeric foam having similar properties of toughness, resilience, flexibility, and thermal insulation. The length 31 includes a pair of spaced apart side-by-side generally cylindrical walls 32 and 33 which define a pair of generally parallel lumens 34 and 35. Connecting the cylindrical walls 32 and 33 is an integral web portion or bight 36.

A first step in the manufacture of the connector is to sever completely one of the cylindrical walls 33 along a transverse plane as at 37 in FIG. 6. The other cylindrical wall 32 remains unsevered or undivided. Adjacent each side of the transverse plane of severance, a portion of the web 36 is removed as illustrated schematically at 38. It is to be understood, of course, that such removal step may follow, precede, or be concurrent with the severing step. Advantageously, the cuts defining the ends of the removed portion 38 are arcuate as illustrated at 39 in FIG. 6. This operation provides the first length of tubing, and specifically the cylindrical wall 33 thereof, with a pair of stub ends 40 and 41.

In FIG. 7 the stub ends 40 and 41 are fitted with flexible polymeric collars 42 and 43, respectively, as by ensleeving. The collars are formed of flexible polymeric material and, in a preferred embodiment, are composed of heat-shrinkable tubing internally coated with a heat-activatable adhesive. Such tubing, capable of shrinking upon exposure to heat, is well known in the art and may be formed of polyethylene or any other suitable polymeric material that is oriented or adapted to shrink radially inwardly when heated to a softening temperature. The internal adhesive coating may be ethyl vinyl acetate or any other conventional adhesive of the type commonly referred to as a "hot-melt" adhesive. When fitted onto the stub ends 40 and 41, the collars have inside diameters slightly larger than the outside diameters of those stub ends; however, upon exposure to heat, the collars are capable of shrinking into tight engagement with the outer surfaces of the stub ends and, because of the heat-activated adhesive coating, becoming permanently secured or bonded to the stub ends.

The stub ends 40 and 41 extend only partway into the collars 42 and 43, leaving space for the insertion of two additional stub ends 44 and 45 provided by a second length 46 of polyurethane foam double-lumen tubing. As shown in FIG. 7, section 46 has had removed therefrom a segment 47 of the web or bight portion 48 so as to provide a second pair of stub ends 44 and 45, Stub ends 44 and 45 are inserted into collars 42 and 43 as illustrated in FIG. 8.

Prior to securing pairs of stub ends together by means of the tubular collars, flexible tubes or conduits 49–51 are inserted through the lumens of the two insulating sections or members 31 and 46. The fluid-carrying tubes or conduits 49–51 may be formed of vinyl or other suitable polymeric material. Tube 49 is inserted through one of the lumens of member 46, through stub ends 45 and 41, and through the lumen of one of the divided sections of severed cylindrical wall 33. Such insertion may occur following or concurrently with the fitting of collars 42 and 43 upon the stub ends of the respective sections or members 31 and 46. The tube 49 is extended beyond the free ends of members 31 and 46 for permanent connection to hermaphroditic coupling elements 18 or 19. Similarly, flexible tube 51 is inserted through the communicating lumens of the other severed section of cylindrical wall portion 33 and the other cylindrical wall portion of member 46. The unsevered cylindrical wall 32 has inserted through its lumen a flexible tube 50.

The assembly depicted in FIG. 8, both before and after the insertion of flexible tubes 49–51, generally assumes a planar configuration when the connector assembly is in a normal unflexed or undeformed state. While such a relationship has been found to be highly effective, anatomical conformability of the connector assembly may be even further enhanced by performing an additional step prior to permanently securing the stub ends 40, 44 and 41, 45 together. Such step consists of rotating or twisting stub ends 40 and 41 in opposite directions as indicated by arrows 40a and 41a in FIG. 8. The extent of such rotation may vary anywhere between approximately 5 degrees to 100 degrees, but preferably closer to about 90 degrees. The effect of such rotation is to shift the cylindrical wall portion 32 of member 31 out of the common plane of wall portions 33, connecting collars 42, 43, and member 46, and into a plane that is parallel with but spaced from that common plane (see FIG. 1). Under such circumstances, the hermaphroditic connectors are also re-oriented, with the connectors or couplings 17 for pads 10, 11 being disposed generally at right angles to the plane of the coupling 17 for joining the Y connector to a fluid source. While stub ends 40 and 41 are held in their rotated positions, the assembly is heated to shrink collars 42 and 43, activate the adhesive lining such collars, and permanently secure stub ends 40 and 44 and stub ends 41 and 45, together.

As indicated above, the ends of tubes 49–51 are each secured in pairs to elements of hermaphroditic couplings 17 so that one such element (i.e., either element 18 or 19) is secured to tubes 49 and 50 at 10' and 10", another such element is secured to tubes 51 and 50 at 11' and 11" and, at the free end of member 46, the end 53 of tube 51 and the end 52 of tube 49 are joined to a third coupling element 18 or 19. A series circuit is created when such coupling elements are mated with the hermaphroditic coupling elements of pads 10 and 11, and with the coupling element of the source of thermal fluid. Thus, tube or conduit 49 may be used to convey thermal fluid to pad 10, tube 50, connected to the outlet of that pad, carries fluid from pad 10 to pad 11, and tube 51, connected to the outlet of pad 11, returns fluid to the source.

As shown clearly in FIG. 1, each pad 10, 11 is provided with double-lumen tubes 10a, 11a leading to an element 18 (or 19) of a hermaphroditic coupling 17. The pads and their tubes may therefore be readily disconnected from, and connected to, the conduit lines of the Y connector 15 by simply uncoupling or coupling the identical mating elements 18, 19 that make up couplings 17. Similarly, the double-lumen tubing that defines conduits 12 and 14 in FIG. 1 terminates at its free end in one element 18 of a hermaphroditic coupling 17 that permits the Y connector to be coupled to or uncoupled from a fluid source.

Of particular significance are the facts that each of the two identical elements 18, 19 that make up each hermaphroditic coupling is non-symetrical (FIG. 4) and that, during manufacture of the Y connector 15, the three elements permanently mounted at the free ends of that connector are oriented to preclude any possibility that a user might inadvertently connect the parts to cause flow therethrough in reverse directions. For example, if the coupling element designated 18 in FIG. 1 is oriented during manufacture so that fluid flow into the Y connector 15 always enters through a lumen 21 of a recessed portion 30 (FIG. 4), and if the two coupling elements at the other two free ends of the Y connector are similarly oriented (so that flow into the Y connector enters through a lumen 21 of a recessed portion 30 and fluid leaving the Y connector exits through a lumen 22 of a projecting portion 28), and if the pads 10, 11 and their coupling elements are oriented in a like manner (i.e., the coupling elements of lines 10a and 11a are oriented so that flow to the pads entered through lumen 21 of recess 30 and flow from the pads exists through lumen 22 of projection 28), then a user cannot connect the parts together in anyway other than the correct way as predetermined at the time of manufacture. The point assumes particular significance where the opposite surfaces of each pad are dissimilar—for example, where one surface is designed for patient contact and the opposite surface is thermally insulated and intended to face away from the patient. Under such circumstances, the orientation of coupling elements 18, 19 established during manufacture of the components eliminates the possibility that a user might connect pads 10, 11 with their insulated non-working surfaces facing inwardly towards the patient.

In the operation of the invention, the arrangement of FIG. 1 is placed on a patient's knee as in FIGS. 2 and 3. The source of thermal fluid may be a conventional control unit including pumping means so as to provide either heating or cooling liquid through the tubes 49–51 through thermal pads 10 and 11. It has been found that the illustrated insulating Y connector conforms well to the contour of a patient's knee without kinking. The kink-free flexing results partly from the fact that the web or bight 36 permits shifting of the various cylindrical walls into different planes. Such a result is readily achieved even when all of the cylindrical wall portions lie in a common plane when the connector is in a normal unflexed state. As brought out above, anatomical conformity without kinking is even further enhanced by rotating stub ends 40 and 41 during assembly so that the unsevered cylindrical wall 32 lies in a different plane than the severed cylindrical wall portions 33 even before the connector is flexed in use. Such rotation also results in a distinctive configuration that effectively directs the user to couple the Y connector 15 to the pad assemblies so that cylindrical wall 32 and the conduit extending through it assume the transversely-extending position designated by numeral 13 in FIG. 1. Since that wall is undivided or unsevered, and since it has no ensleeving collar 42 or 43, it readily assumes the smoothly-curved kink-resisting arcuate configuration depicted in the drawings.

While in the foregoing specification a detailed description of an embodiment of the invention has been set down for purposes of illustration, many variations in the details hereingiven may be made by those skilled in the art without departing from the spirit and scope of the invention.

I claim:

1. An insulating, anti-kinking Y connector for conducting a thermal fluid between a source and a pair of heating/cooling pads for thermal treatment of a patient following arthroscopic surgery or the like, comprising first and second members of flexible, resilient, thermal-insulating material each having two parallel cylindrical walls defining a pair of parallel lumens with said cylindrical walls of each member being connected by an integral web; one of said cylindrical walls of said first member being continuous for the full length of said first member and the other of said cylindrical walls of said first member being divided along a transverse plane, with portions of said web removed on each side of said transverse plane, to provide a pair of first stub ends; said second member having a portion of its web removed adjacent one end thereto to provide a pair of second stub ends; connecting means joining each one of said first stub ends with one of each of said second stub ends; flexible tubes for carrying fluid extending through the lumens of said members; said Y connector having three free end portions each provided with a double-lumen coupling element joined to and communicating with said flexible tubes for detachably coupling said Y connector to mating elements of a pair of pads and a fluid source.

2. The connector of claim 1 in which said connecting means comprises a pair of collars ensleeving and joining together one each of said first and second stub ends.

3. The connector of claim 2 in which said collars are adhesively secured to said first and second stub ends.

4. The connector of claims 2 or 3 in which said collars join said first and said second stub members to hold said stub ends in a plane generally parallel with but spaced from a plane extending along the axis of said continuous wall of said first member when said connector is in a normal unflexed state.

5. The connector of claim 1 in which said first member has a pair of free end portions and said second member has a single free end portion; a pad coupling element joined to the flexible tubes of said first member at each of said free end portions thereof; and a fluid source coupling element connected to said flexible tubes at said single free end portion of said second member.

6. The connector of claim 5 in which each of said coupling elements includes a block-like body having first and second lumens extending therethrough; each body having a hermaphroditic end adapted to be coupled to the hermaphroditic end of an identical coupling element; said hermaphroditic end of each of said bodies including a stepped end wall with a first wall portion being equipped with a longitudinally-extending tubular projection aligned with said first lumen; said hermaphroditic end also including a second wall portion having a longitudinally-extending recess aligned with said second lumen sized to receive said tubular projection of an identical hermaphroditic coupling element.

7. The connector of claim 6 in which each body lumen of said coupling element is equipped with a poppet valve positioned and arranged for opening said lumens when said coupling element is coupled to an identical coupling element.

8. A method of making a Y connector for arthroscopic surgery and the like, comprising the steps of
providing first and second lengths of resilient, flexible, double-lumen tubing of thermal insulating material each having a pair of generally cylindrical walls disposed in parallel spaced-apart relation with said pair of walls being connected together in adjacent portions by an integral web;
completely severing one of said cylindrical walls of said first length of tubing along a transverse plane and removing a portion of said web adjacent said plane to provide a first pair of stub ends, while leaving the other of said cylindrical walls of said first length in unsevered condition;
removing a portion of said web of said second length of double lumen tubing adjacent one end thereof to provide a second pair of stub ends;
and permanently securing said first pair of said stub ends to said second pair of stub ends.

9. The method of claim 8 in which conduit means is inserted into each lumen of each cylindrical wall whereby conduit means in the lumen of the unsevered cylindrical wall of said first length of tubing is adapted for interconnecting a pair of thermal pads and said conduit means in each of said interconnecting stub end lumens is adapted for interconnecting a source of thermal fluid to each of such pads with one interconnected pair of stub ends constituting a supply line to one thermal pad and the other interconnected pair of stub ends constituting a return line from the other thermal pad to said source.

10. The method of claim 9 in which said stub ends of said first length are rotated in opposite directions about the axes of the respective lumens thereof prior to securing said first pair of stub ends to said second pair, thereby displacing said unsevered cylindrical wall of said first length out of a plane common to said severed cylindrical wall and said second length of tubing.

11. The method of claim 10 in which said rotating and securing steps are performed after insertion of said conduit means.

12. The method of claim 11 in which said rotating step comprises oppositely rotating each of the stub ends of said first pair an angular distance within the range of approximately 5 to 100 degrees.

13. The method of claims 9, 10, or 11 in which said securing step comprises ensleeving the stub ends of said first and second lengths within tubular collars of heat-shrinkable polymeric material internally coated with a heat-activatable adhesive; and thereafter heating said collars to shrink the same and adhesively secure said stub ends together.

14. The method of claim 8 in which there are the further steps of inserting three flexible conduits into and through the lumens of said cylindrical walls to define flow passages extending between three free ends of said Y connector with the ends of said conduits projecting in pairs at said free ends; and attaching coupling elements to said projecting ends of said conduits at said three free ends of said Y connector.

15. The method of claim 14 in which all of said coupling elements are identical and each is non-symetrical with a first lumen extending through a first end portion and a second lumen extending through a differently-shaped second end portion; said attaching step including identically orienting said coupling elements so that flow therethrough into said Y connector enters through said first lumen and flow therethrough out of said Y connector exits through said second lumen.

16. An insulating, anti-kinking Y connector for conducting a thermal fluid between a source and a pair of heating/cooling pads for thermal treatment of a patient following arthroscopic surgery or the like, comprising first and second members of flexible, resilient, thermal-insulating material each having two parallel cylindrical walls defining a pair of parallel lumens with said cylindrical walls of each member being connected by an integral web; one of said cylindrical walls of said first member being continuous for the full length of said first member and the other of said cylindrical walls of said first member being divided along a transverse plane, with portions of said web removed on each side of said transverse plane, to provide a pair of first stub ends; said second member having a portion of its web removed adjacent one end thereof to provide a pair of second stub ends; connecting means joining each one of said first stub ends with one of each of said second stub ends; flexible tubes for carrying fluid extending through the lumens of said members; said Y connector having three free end portions each provided with a double-lumen coupling element joined to and communicating with said flexible tubes for detachably coupling said Y connector to mating elements of a pair of pads and a fluid source; each coupling element being non-symetrical with a first lumen extending through a first end portion and a second lumen extending through a differently-shaped second end portion; and all of said coupling elements of said Y connector being identically oriented with flow into said Y connector being through said first lumen of each coupling element and flow out of said Y connector being through said second lumen of each coupling element.

17. The connector of claim 16 in which said first end portion of each coupling element includes a projection and said second end portion of each coupling element includes a recess.

18. The connector of claims 16 or 17 in which a pair of thermal pads are detachably connected to said Y connector; each pad including a double-lumen tube having a coupling element at one end thereof identical to and adapted to mate with said coupling elements of said Y connector.

* * * * *